United States Patent [19]

Ricketts et al.

[11] 4,026,278
[45] May 31, 1977

[54] ELECTRODE POSITIONING AND RETAINING BELT

[75] Inventors: James R. Ricketts, Milwaukee, Wis.; Corrine M. Ballantine, Burlington, Canada; Gerald J. Reiser, Milwaukee, Wis.

[73] Assignee: Marquette Electronics, Inc., Milwaukee, Wis.

[22] Filed: Nov. 6, 1975

[21] Appl. No.: 629,596

[52] U.S. Cl. .......................... 128/2.06 E; 128/388; 128/418; 128/DIG. 4
[51] Int. Cl.² ......................................... A61B 5/04
[58] Field of Search ...... 128/2.06 E, 2.1 E, DIG. 4, 128/DIG. 15, 404, 405, 410, 411, 416-418, 384, 385, 388

[56] References Cited
UNITED STATES PATENTS

| 2,943,628 | 7/1960 | Howell | 128/418 |
|---|---|---|---|
| 3,542,010 | 11/1970 | Love | 128/2.1 E |
| 3,612,061 | 10/1971 | Collins | 128/418 |
| 3,702,613 | 11/1972 | Panico et al. | 128/417 |
| 3,888,240 | 6/1975 | Reinhold, Jr. et al. | 128/2.1 E |
| 3,896,790 | 7/1975 | Dikmen | 128/2.1 B |

OTHER PUBLICATIONS

Barr et al., "A device for rapid ECG monitoring", Anathesia, vol. 27, No. 1, Jan. 72, pp. 94-96.
Richardson et al., "Some New Electrode... Monitoring," Aerospace Medicine, July 1968, pp. 745-750.

*Primary Examiner*—Robert W. Michell
*Assistant Examiner*—Lee S. Cohen
*Attorney, Agent, or Firm*—Andrus, Sceales, Starke & Sawall

[57] ABSTRACT

An electrode positioning belt has Velcro loop fabric along the inner surface. Velcro hook fabric may be affixed to the back of the electrodes so they may be removably secured to the belt. In another embodiment the electrodes may be snapped through holes in the belt. The belt is wrapped around a body member. The ends of the belt overlap and a tab of hook fabric at one end of the belt on the outer surface is used to secure the belt.

3 Claims, 5 Drawing Figures

U.S. Patent May 31, 1977 4,026,278
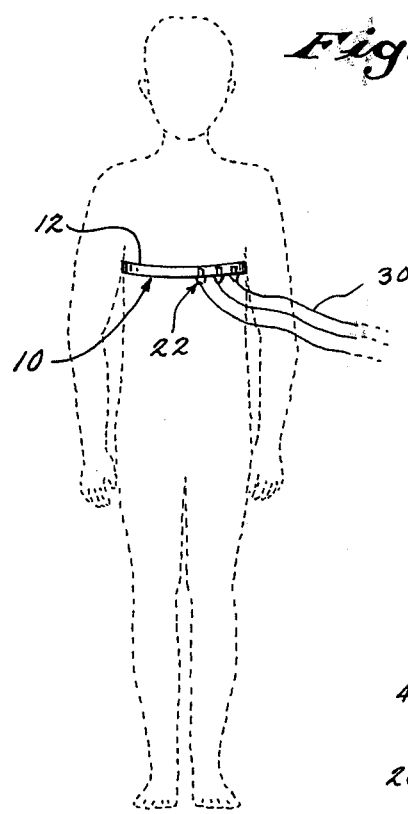
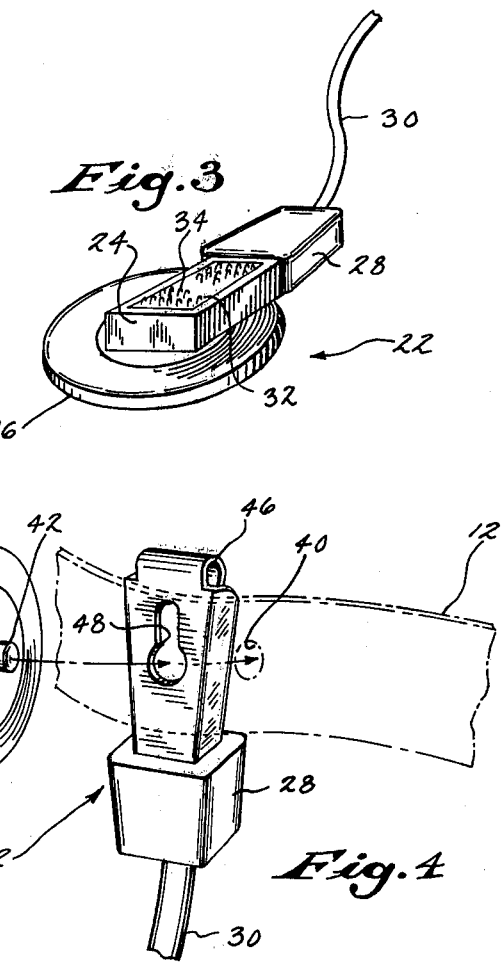
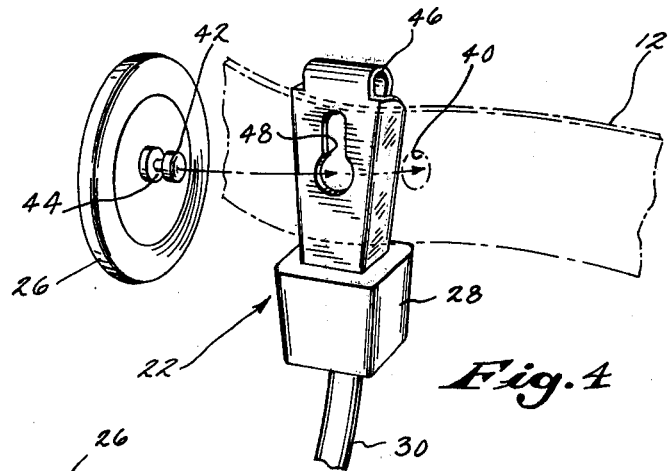
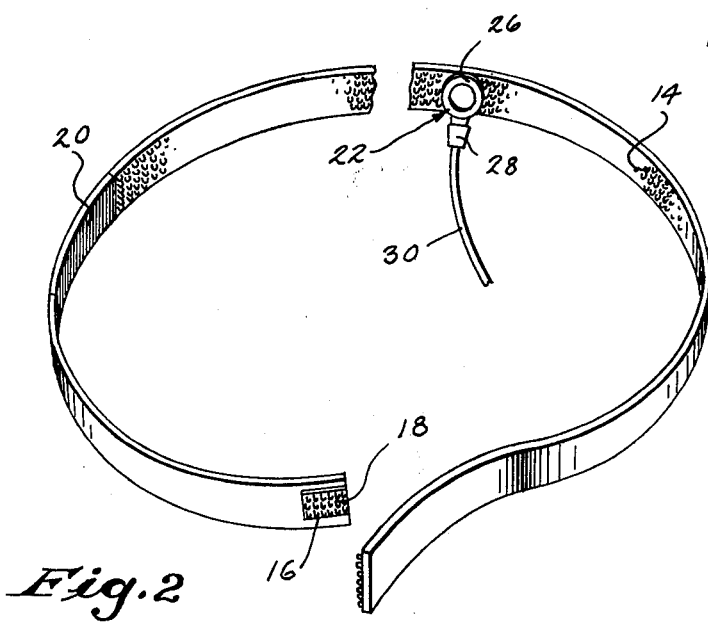
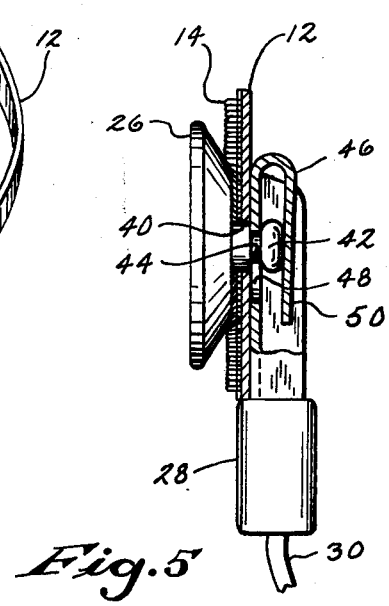

ELECTRODE POSITIONING AND RETAINING BELT

BACKGROUND OF THE INVENTION

1. Field of the Invention

The present invention relates to a belt for applying sensory electrodes to the body.

2. Description of the Prior Art

In order to ascertain electrical phenomena arising from physiological functioning, for example, the electrocardiographic data associated with the functioning of the heart, it is necessary to apply sensory devices to the skin. There devices are commonly termed "electrodes". Usually a plurality of electrodes are employed to measure potentials between a plurality of points on the body.

In the past, it has been common to apply each electrode individually and to employ means which directly affix the electrodes to the skin. This is most commonly a means which retains the electrode on the skin by suction.

However, there are a number of circumstances in which such an arrangement is both ineffective and inappropriate. For example, the body movements of infants render the application and retention of conventional electrodes difficult. In other applications, such as monitoring, it is necessary to periodically obtain repetitious samples of electrical data for comparative purposes. With individually applied electrodes it is difficult, if not impossible, to insure that the electrodes are repeatedly positioned at the same location so as to insure the validity of the sampled data. In screening applications, it is desired to apply and remove the electrodes as rapidly as possible. This is difficult with individually applied electrodes.

, SUMMARY OF THE PRESENT INVENTION

It is, therefore, the object of the present invention to provide an improved means for rapidly and securely applying electrodes to a body member. The invention is capable of accurately applying a plurality of electrodes throughout a series of repetitious applications.

Briefly, the present invention contemplates a belt having a length sufficient to encircle the body member. The belt has a surface exposing a first type of fastener fabric, for example of the Velcro loop type, on one side thereof and a surface portion of a second fastener fabric type, for example Velcro hook type, adjacent an end of the other side. This permits the belt to be removably secured to the body member by engaging the first fastener fabric surface with the second fasterner fabric surface. The belt may contain an elastic section for retaining the belt on the body member.

The electrodes exhibit a surface of the second fastener fabric type for removably attaching said electrode to the exposed surface of said belt. In the alternative, the electrodes may be snapped through holes in the belt.

BRIEF DESCRIPTION OF THE DRAWING

FIG. 1 is a schematic view of the present invention showing its use in retaining and positioning electrodes on the body.

FIG. 2 is a perspective view of the belt portions of the present invention.

FIG. 3 is a perspective view of one embodiment of the electrode portion of the present invention.

FIG. 4 is an exploded perspective view of another embodiment of the electrode and belt portions of the present invention.

FIG. 5 is a cross sectional view of the embodiment of FIG. 4.

DESCRIPTION OF THE PREFERRED EMBODIMENT

Turning now to the Figures, there is shown in FIG. 1 the electrode applying and positioning means 10 of the present invention as applied to the chest of the human body. The present invention employs a releasably engageable fastener fabrics sold under the trademark Velcro. Such a fastener includes a first fabric which consists of a deep pile of loops of plastic thread on a cloth backing. A second fabric consists of a cloth having a plurality of relatively stiff plastic thread hooks extending therefrom. Pressing the two fabrics together inserts the loops in the hooks, thereby joining the two cloth backing together. The backings may be attached to the objects to be joined. Separating forces applied normal to the fabric disengages the hooks from the loops and parts the cloth backings.

As shown in FIG. 2, means 10 includes belt 12 of an appropriate width and of a length suitable for encircling the body member to which the electrodes are to be applied. Belt 12 comprises or has applied to the inner surface of it one type of the fastener fabric 14. It has been found preferable to employ the loop type fabric on the inner surface of belt 12. On the other side of belt 12, adjacent one end thereof, a small portion 16 of hook fabric 18 is fastened. This enables belt 12 to be formed into a loop about the body member by pressing the portion 16 of hook fabric 18 on one side of belt 12 into loop fabric 14 on the other side of belt 12. If desired, belt 12 may include an elastic section 20, in a location at which electrodes will not be positioned, which assists in retaining belt 12 on the body member.

Electrodes 22 include base 24 having electrically conductive disk 26 mounted thereon. Disk 26 is coupled to connector 28 and lead wire 30 for connection to diagnostic equipment such as an electrocardiograph, not shown. A small portion 32 of hook fabric 34 is affixed to base 24, as shown most clearly in FIG. 3.

In use, electrodes 22 are positioned along belt 12 at desired locations by pressing hook fabric 34 attached to the back of electrodes 22 into the loop fabric 14 of belt 12. The belt is then wrapped around the body member at the desired location with the electrodes against the body and the belt is secured by pressing the hook fabric 18 of portion 16 into the loop fabric 14 of belt 12.

The electrodes 20 may be repositioned on belt 12 by pulling the electrode off the belt and pressing it back onto the belt at the newly desired location. Electrodes may be added or removed in the same manner. Belt 12 may be marked to assist in positioning electrodes 20 at standard locations for particular body members. Adjustments to these positions for differently sized body members may also be indicated.

An alternative embodiment of the invention is shown in FIGS. 4 and 5. This embodiment has been found useful with a short belt 12, for example, one designed to fit around the ankle, in that it reduces the bulge under the belt produced by the electrode. In this embodiment, holes are provided in belt 12 in the locations at which the electrodes are to be positioned. FIG. 4 shows such a belt 12 having hole 40. Disk 26 has a stud 42 on the back containing groove 44. Stud 32 fits through hole 40 in belt 12. Electrode base 46 is formed of sheet metal and includes keyhole slot 48 for receiving groove 44 of stud 42 in the narrower portion of the slot. Tab 50 presses against the end of stud 42 to retain the tab in the slot, as shown in FIG. 5.

Belt 12 is removed by pulling portion 16 of hook fabric 18 out of loop fabric 12 on the inner surface of belt 12.

Various modes of carrying out the invention are comptemplated as being within the scope of the following claims particularly pointing out and distinctly claiming the subject matter which is regarded as the invention

We claim:

1. Apparatus suitble for removably affixing electrocardiographic electrode elements to a body member for providing electrocardiographic signals, said apparatus employing first and second engageable fastener surfaces of the hook and loop pile type and comprising:
    a belt having a length sufficient to encircle the body member, said belt having an exposed surface of the first fastener type on the inner side thereof abuttable with the body member when the apparatus is in use, said belt having a surface portion of the second fasterner type on the outer said thereof adjacent an end of the outer side removably securing the belt to the body member by engaging the first fastener type surface with the second fastener type surface; and
    a plurality of electrode elements, each of the electrode elements including a surface of the second fastener type electrode elements being thereon, each of the removable thereon attached by the second fastener type thereon, each of the electrode elements being removably attached by the second fastener type surface thereon at a desired location on the exposed surface of the inner side of said belt, said electrode elements including means for connection to electrocardiographic signal responsive equipment.

2. The apparatus according to claim 1 wherein said first fastener type is of the loop type and said second fastener type is of the hook type.

3. The apparatus according to claim 1 wherein the surfaces of the hook and loop pile type comprise fastener fabrics of the hook and loop pile type affixed to said belt and electrode elements.

* * * * *